(12) United States Patent
Phelan et al.

(10) Patent No.: US 7,552,650 B2
(45) Date of Patent: Jun. 30, 2009

(54) GRIPPING FIXTURE

(75) Inventors: James Joseph Phelan, Athenry (IE); Matthew Coates, Boston, MA (US)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 280 days.

(21) Appl. No.: 11/736,447

(22) Filed: Apr. 17, 2007

(65) Prior Publication Data

US 2008/0257061 A1    Oct. 23, 2008

(51) Int. Cl.
G01N 3/02 (2006.01)
G01N 3/08 (2006.01)
B66C 1/46 (2006.01)
B66C 1/54 (2006.01)
B66C 1/42 (2006.01)

(52) U.S. Cl. .............................. 73/856; 73/818; 73/824; 294/119.3; 294/98.1; 294/93

(58) Field of Classification Search .................... 294/93, 294/98.1, 119.3; 73/856, 818, 824
See application file for complete search history.

(56) References Cited

U.S. PATENT DOCUMENTS 4,445,323 A * 5/1984 Wuermli .................. 294/119.3
6,494,516 B1 * 12/2002 Bertini ........................ 294/93
2007/0088368 A1 * 4/2007 Acosta et al. .............. 623/1.11

OTHER PUBLICATIONS

American Society for Testing and Materials, "ASTM F2394—07", Annual Book of ASTM Standards, Section 13. Medical Devices. pp. 1413-1425. Published Sep. 2008. Accessed Feb. 19, 2009.*

* cited by examiner

*Primary Examiner*—Lisa M Caputo
*Assistant Examiner*—Jonathan Dunlap
(74) *Attorney, Agent, or Firm*—Fulwider Patton LLP

(57) ABSTRACT

A gripping fixture suitable for use in stent securement testing is described. The gripping fixture includes a housing having a chamber, a rigid perforated tubular member positioned within the chamber, a multiplicity of radially extending pins arranged to slide in the perforations in the tubular member, and an elastic sheath that circumscribes the outer ends of the pins and surrounds the tubular member. A pressure chamber is formed between the housing and the elastic sheath. The gripping fixture also includes a pressure controller for controlling the pressure within the pressure chamber. The pressure applied in the pressure chamber acts on the elastic sheath and may be used to cause some of the pins to engage a stent during the stent securement test to hold the stent in place relative to the gripping fixture while the tensile force required to dislodge the stent from a catheter is measured.

20 Claims, 3 Drawing Sheets

GRIPPING FIXTURE

FIELD OF THE INVENTION

The present invention relates generally to devices suitable for use in gripping tubular work pieces. In one aspect, the present invention relates to an assembly that holds a stent during stent securement testing.

BACKGROUND OF THE INVENTION

Stents and stent delivery assemblies are utilized in a number of medical procedures. As such, their general structure and function are well known. Stents are generally cylindrical prostheses introduced, via a catheter, into a lumen of a body vessel. Typically, the stent is secured to the catheter in a configuration having a generally reduced diameter for transport and delivery. Once the stent is positioned at a desired location in a target vessel it is deployed by expanding the stent to the diameter of the target vessel. In its expanded configuration, the stent supports and reinforces the vessel walls while maintaining the vessel in an open, unobstructed condition.

Balloon expandable stents are well known and widely available in a variety of designs, diameters and configurations. Balloon expandable stents are crimped to their reduced diameter about a delivery catheter, then maneuvered to the deployment site and expanded to the vessel diameter by inflation of a balloon positioned between the stent and the delivery catheter.

During advancement of the stent through a body vessel to a deployment site, the crimped stent must securely maintain its axial position on the delivery catheter. That is, the crimped stent must not slide proximally or distally along the catheter during advancement, and especially must not dislodge from the catheter. Stents that are not properly crimped, secured or retained to the delivery catheter may slip thereby becoming lost, damaged, deployed in the wrong location or only partially deployed.

Therefore, techniques have been developed to test the tensile force required to dislodge the balloon and catheter from the crimped stent. Although such stent securement tests are generally known, there are continued efforts to develop improved stent securement testing devices and techniques.

SUMMARY OF THE INVENTION

The present invention provides an apparatus and methods suitable for use in stent securement testing. In one embodiment, a gripping fixture is described that includes a housing having a chamber. A rigid perforated tubular member is positioned within the chamber and a multiplicity of radially extending pins are arranged to slide in the perforations in the tubular member. An elastic sheath circumscribes the outer ends of the pins and surrounds the tubular member. Together, the elastic sheath and housing form a pressure chamber. The gripping fixture additionally includes a pressure controller for controlling the pressure within the chamber.

The pressure applied in the pressure chamber acts on the elastic sheath and may be used to move the outer ends of the pins causing the pins to slide radially through the rigid perforated tubular member. In doing so, the pins may engage a stent positioned within the tubular member. In one embodiment, the stent includes a plurality of struts and applying pressure in the pressure chamber causes some of the pins to pass into gaps between adjacent struts. The pins hold the stent in place relative to the gripping fixture during the stent securement test.

In another embodiment, a method of stent securement testing is described. A stent is crimped around the distal end of a catheter. The catheter is then positioned on a tensile force test bench. The distal end of the catheter is then placed in a gripping fixture having a multiplicity of pins. Pressure is applied to the gripping fixture to cause the pins to engage the stent. The catheter is then moved relative to the gripping fixture to pull the catheter away from the gripping fixture. The pins of the gripping fixture hold the stent in place relative to the gripping fixture during the stent securement test while the tensile force required to dislodge the stent from the catheter is measured.

BRIEF DESCRIPTION OF THE DRAWINGS

For a better understanding of the invention, reference should be made to the following detailed description taken in conjunction with the accompanying drawings, in which.

In the drawings, like reference numerals are used to designate like structural elements. It should also be appreciated that the depictions in the figures are diagrammatic and not to scale.

DETAILED DESCRIPTION

Figure 1:
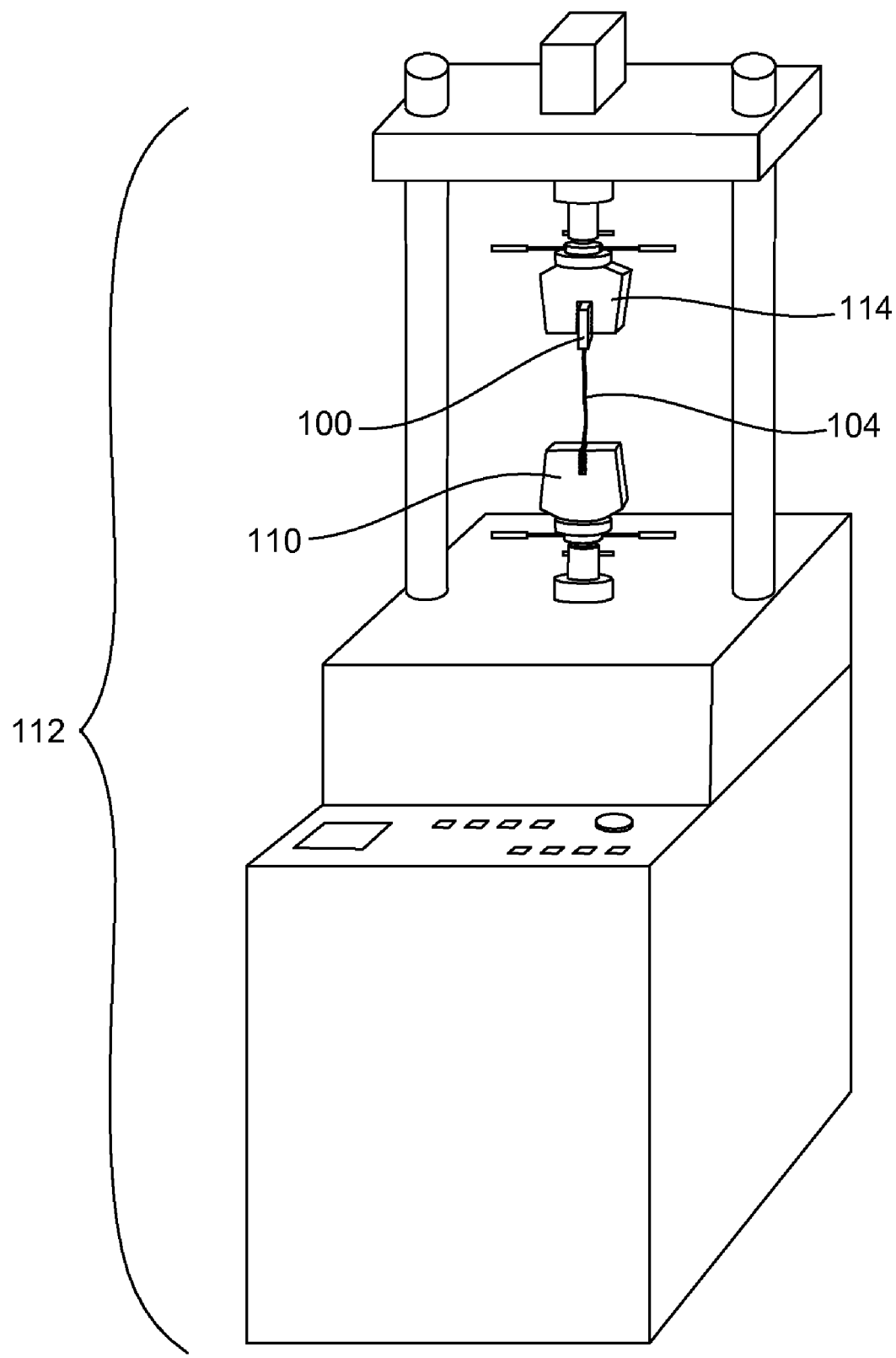
FIG. 1 illustrates a system for performing a tensile force measurement that incorporates a gripping fixture in accordance with an embodiment of the present invention.

While the present invention will be described with reference to a few specific embodiments, the description is illustrative of the invention and is not to be construed as limiting the invention. Various modifications to the present invention may be made to the preferred embodiments by those skilled in the art without departing from the true spirit and scope of the invention as defined by the appended claims. It is additionally noted, that for a better understanding, like components are designated by like reference numerals throughout the various figures.

Figure 2:
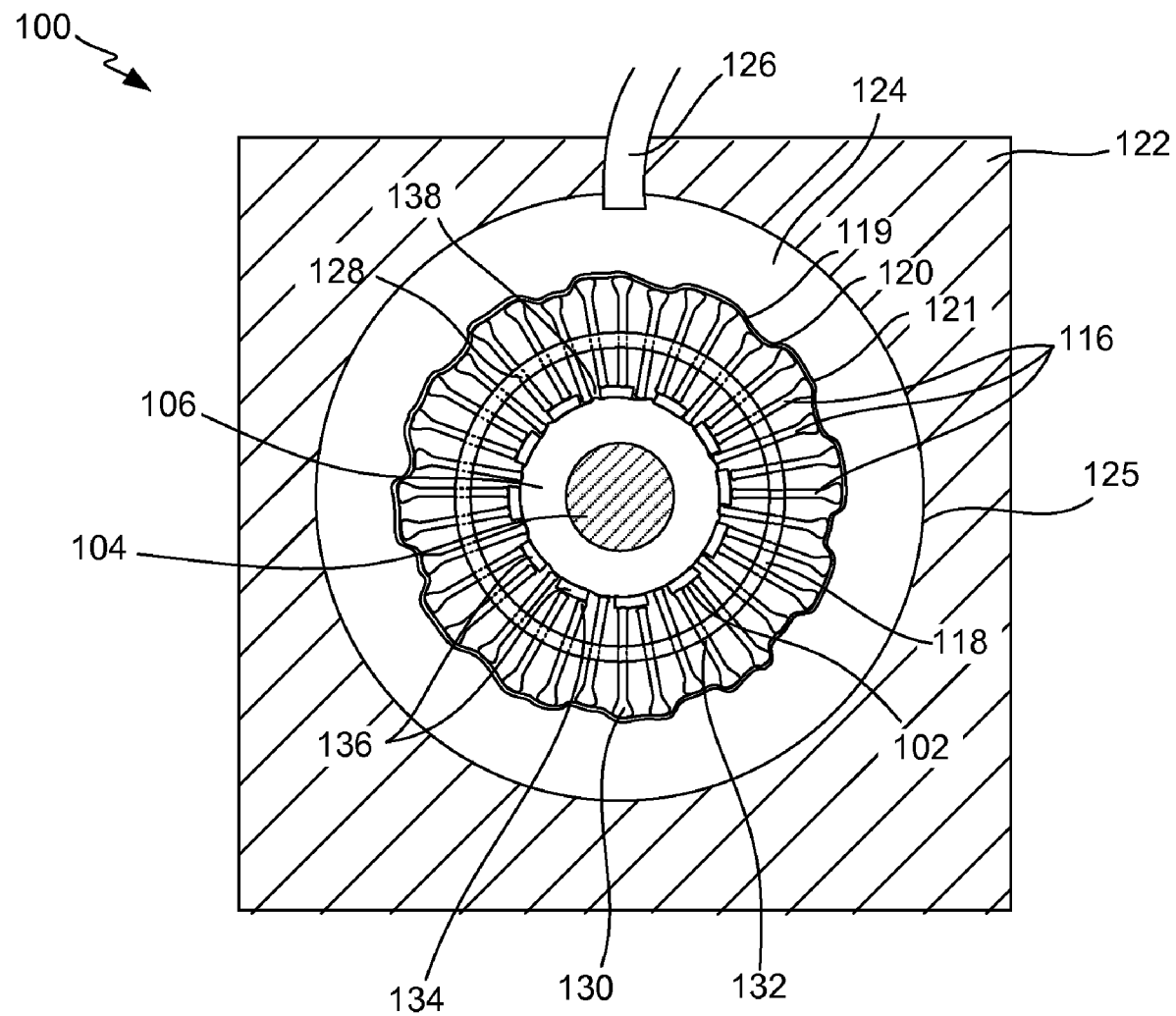
FIG. 2 illustrates a diametric cross section of a gripping fixture in accordance with an embodiment of the present invention.
Figure 3:
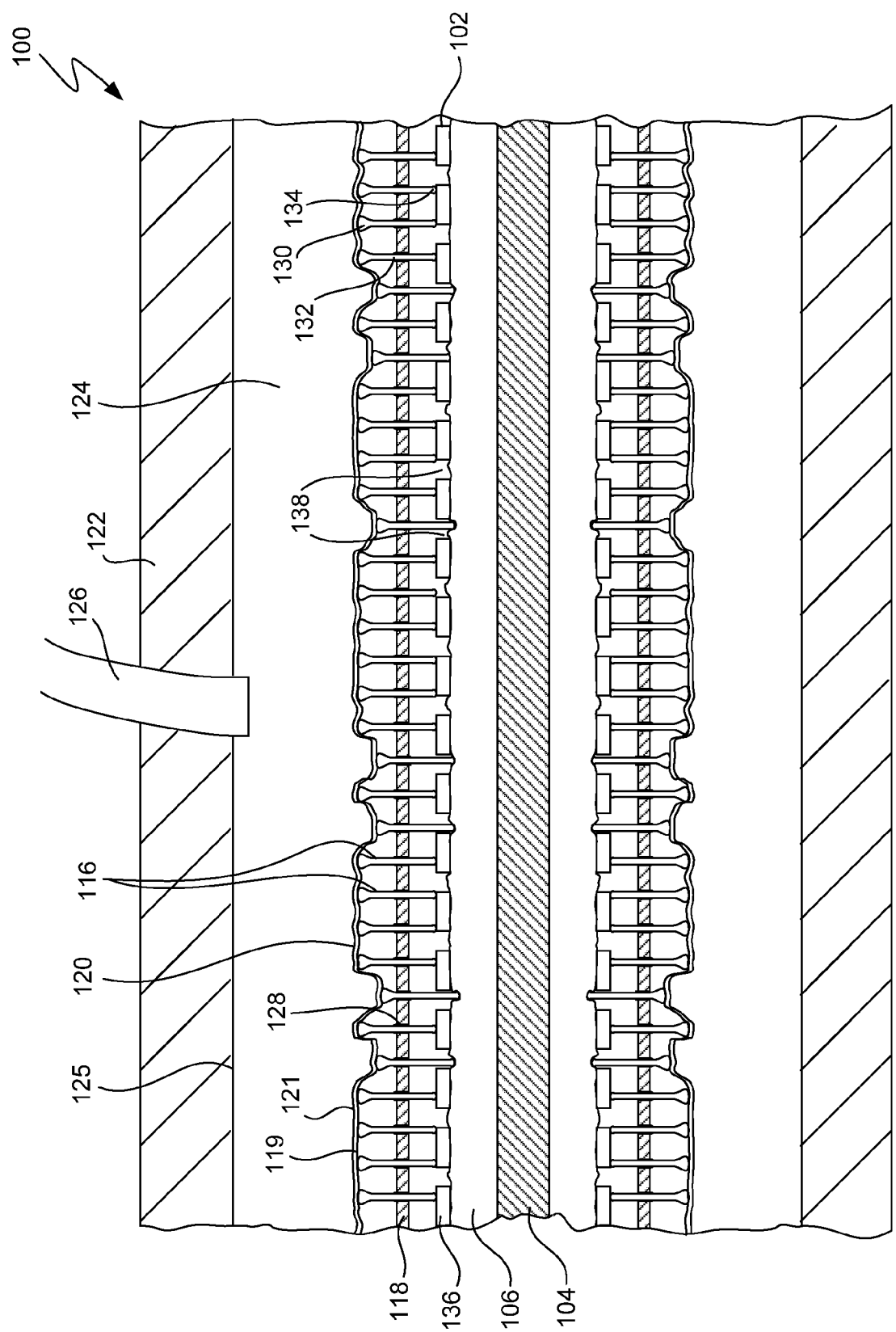
FIG. 3 illustrates an axial cross section of a gripping fixture in accordance with an embodiment of the present invention.

Referring now to FIGS. 1-3, a gripping fixture 100 suitable for use in holding a stent 102 in place during a stent securement test is described. More particularly, the gripping fixture 100 is arranged to prevent axial movement of the stent 102 relative to the gripping fixture. In the described embodiment, the stent 102 is a balloon-expandable stent, although it should be appreciated that the invention may be practiced on alternative stent varieties as well. In the embodiments that follow, the gripping fixture 100 is described in the context of a stent securement test. Such testing is well known in the art. ASTM F2394, "Standard Guide for Measuring Securement of Balloon Expandable Stent Mounted on Delivery System," provides guidance for carrying out a stent securement test. In a representative test, the axial tensile force required to dislodge a stent 102 from a catheter 104 is measured. The gripping fixture 100 is configured to engage the stent without further pressing the stent 102 onto the catheter 104 appreciably. This helps minimize the effect that the test fixture has on the interaction between the stent and the catheter during securement testing. In this manner, a more accurate force measurement may be achieved.

In an exemplary stent securement test, a stent 102 is positioned over and crimped around the balloon region 106 at the distal end of a balloon catheter 104. The proximal end of the balloon catheter 104 is constrained to an anchor 110 of a test bench 112 configured to measure tensile force. An exemplary test bench is illustrated in FIG. 1. The stent 102 is positioned inside the gripping fixture 100, which is used to hold the stent in place. The gripping fixture 100 is, in turn, constrained to a second anchor 114 of the test bench 112. One of the two anchors 110 or 114 is coupled with a load cell. By way of example, a strain gauge-based load cell may be employed in the test bench 112 to measure tensile force. During the tensile force measurement, one anchor is generally moved relative to the other to increase the displacement between the two anchors. The growing displacement results in an increasing axial tensile force that attempts to pull the balloon catheter 104 from the stent. Generally, the stent 102 is eventually dislodged from the balloon 106 and the measurement ends. The test bench includes software or other means to measure the tensile force acting on the catheter 104 and stent 102 during the measurement.

When performing the measurement, it is desirable to hold the stent 102 rigidly in place relative to the gripping fixture 100. Furthermore, to achieve a more accurate measurement, the gripping fixture 100 should hold the stent 102 while not further compressing the stent around the balloon 106. Further compression of the stent may increase the frictional forces between the gripping fixture 100 and the balloon 106 beyond that which is intended, and would thus interfere with the accuracy of the measurement. More particularly, this would result in a falsely high force measurement. Additionally, it is desirable to minimize the effect of any engagement between the gripping fixture 100 and the balloon 106. More particularly, the gripping fixture 100 should be arranged so that it does not appreciably resist the movement of the catheter 104 out of the stent 102, which would also interfere with the accuracy of the measurement.

To facilitate these and other objectives, the gripping fixture 100 includes a large number of pins 116, a perforated rigid tubular member 118 and an elastic sheath 120, as illustrated in FIGS. 2-3. The perforated rigid tubular member 118 is arranged to accommodate the length and diameter of the stent 102 such that the stent may be positioned within the rigid tubular member 118. In general, the rigid tubular member 118 is preferably sized to accommodate a variety of stents having varying diameters and lengths. In a preferred embodiment, the rigid tubular member 118 is at least as long as the stent 102 positioned within it so that the entire stent may be enclosed within the tubular member 118.

The gripping fixture 100 includes a high density of pins 116 that are arranged to slide radially in and out of the perforated rigid tubular member 118. By way of example, an appropriate density of pins 116 may be as high as or even exceed 100 pins per square cm. In one embodiment, it may be desirable to have a density of pins 116 that meets or exceeds the density of gaps 138 formed in between the lattice of stent struts 136 that form the stent 102. Generally, the density of the pins 116 may vary according to the size and density of the gaps 138 formed in between the stent struts 136.

The elastic sheath 120 preferably has approximately the same length as the rigid tubular member 118 and is sized so as to circumferentially surround the rigid tubular member 118 as well as the pins 116. The elastic sheath 120 may be formed from a number of suitable elastic materials. By way of example, the elastic sheath 120 may be formed from silicone, latex, polyurethane, or other suitable polymeric materials. In one embodiment, the elastic sheath 120 is in the form of an elastic tube having a circular cross-section. In another embodiment, the elastic sheath 120 does not have a well-defined structure with a consistent cross section.

The gripping fixture 100 additionally includes a housing 122 that is preferably sized to enclose the stent 102, the tubular member 118 and the elastic sheath 120. The housing 122 may be formed from any suitable material. By way of example, rigid materials such as a metals, metal alloys, ceramic or hard polymeric materials work well. The length of the housing is also preferably approximately equal to that of the tubular member 118. In one embodiment, the tubular member 118 is rigidly secured with the housing 122. The elastic tube 120 is also secured with the housing 122 such that a sealed pressure chamber 124 is formed between the outer surface of the elastic sheath 121 and the inner surface 125 of the housing. The housing 122 additionally includes an inlet 126. The inlet 126 is configured to introduce pressurized fluid into the sealed chamber 124. In one embodiment, the fluid may be a gas such as compressed air. In an alternate embodiment, the fluid may be a liquid such as water.

The diameters of the pins 116 should only be slightly larger than the diameters of the associated through holes 128 in the rigid tubular member 118 that the pins slide through. More particularly, it is desired that the diameters of the through holes 128 and pins 116 be as close as possible (but outside of each other's range of tolerances) such that the pins 116 are essentially restricted to one-dimensional motion within the through holes 128. In one embodiment, the outer ends 130 (relative to the longitudinal axis of the rigid tubular member 118) of the pins 116 are attached to the inner surface of the elastic sheath 120. By way of example, the outer ends 130 may be attached to the inner surface 119 of the elastic sheath 120 with a suitable adhesive. To facilitate this, the outer ends 130 of the pins 116 may have larger diameters than the diameters of the associated middle portions 132 of the pins. Larger outer end diameters may also reduce the likelihood that the elastic sheath 120 is punctured by the pins 116.

Prior to the axial force measurement, the stent 102 is first crimped around the balloon catheter 104 with a suitable crimping device. The crimped stent 102 is then positioned within the perforated rigid tubular member 118. FIGS. 2 and 3 illustrate diametric and axial cross sections, respectively, of the crimped stent 102 and catheter 104 positioned within the rigid tubular member 118 of the gripping fixture 100. A pressure controller is then used to elevate the pressure of the gas (or other suitable fluid) in the sealed pressure chamber 124 via the introduction of compressed gas through the inlet 126. By way of example, pressures in the range of approximately 0 to 20 psi should work well. In other applications, higher pressures may be required. By way of example, some high pressure applications may necessitate pressures in the range of 50 to 200 psi or higher. The elevated pressure of the gas results in a radial force that pushes on the outer surface of the elastic sheath 118. This causes the elastic sheath 118 to contract. The elastic sheath 118, in turn, exerts a radial force on the outer ends 130 of the pins 116 causing the pins to slide radially inward through the rigid tubular member 118. Given the high density of pins, when sufficient pressure is applied, at least a substantial portion of the pins will slide through the gaps 138 in between the struts 136. A portion of the pins may also engage the struts 136 and catheter 104 as well.

In another embodiment, the elastic sheath may already be in an expanded state prior to positioning the crimped stent within the tubular member 118. In this embodiment, the pressure controller is used to provide a pressure in the pressure chamber 124 that is lower than the outside room pressure. In this way, the room pressure expands the elastic sheath 120 to a diameter that is greater than its equilibrium diameter. After the stent 102 and catheter 104 are positioned within the tubular member 118, the pressure controller elevates the pressure in the pressure chamber 124 to a pressure at or above room pressure. Again, this results in contraction of the elastic sheath 120 to its equilibrium state (or beyond), which then results in the pins sliding radially inward. In this manner, the elastic sheath's equilibrium diameter may be sufficiently small such that the pins 116 may pass into the gaps 138.

As already described, it is desirable that the pins 116 are appropriately spaced apart and sized in diameter such that a substantial portion of the pins slide through the gaps 138 formed in between the struts 136 that form the stent 102. By way of example, a pin center to pin center spacing in the range of approximately 0.1 to 5.0 mm and a pin diameter in the range of approximately 0.05 to 3.0 mm should work well for a variety of stent geometries. In this manner, statistically speaking, when the catheter 104 and gripping fixture 100 are pulled apart during the axial force measurement, the sides of a substantial portion of the pins 116 will contact the sides of the stent struts 136. In this way, the pins 116 prevent further axial movement of the stent out of the gripping fixture 100.

Some of the inner ends 134 of the pins 116 may contact the catheter 104 depending upon the thickness of the struts 136, the pressure in the chamber 124, and the elasticity of the elastic sheath 120. It should be noted, statistically speaking, that at least some of the inner ends 134 of the pins 116 will engage the struts 136 of the stent 102. Since at least some pins 116 will engage the stent struts 136, the remainder of the pins not engaging stent struts will be limited in their travel through the through holes 128 in the rigid tubular member 118 and subsequently through the gaps 138 in between the stent struts 102. In one embodiment, if the struts 136 are sufficiently thick, the elastic sheath 120 is sufficiently stiff and/or the pressure in the chamber 124 is sufficiently low, then virtually none of the pins 116 may contact the catheter 104. In this situation, any pins 116 that do contact the catheter 104 will do so lightly and will thus have a minimal impact on the accuracy of the force measurement. On the other hand, if the struts 136 are sufficiently thin, the elastic sheath 120 is sufficiently elastic and/or the pressure in the chamber 124 is sufficiently high, then many of the pins 116 may contact the catheter 104. In this manner, for a given stent and elastic sheath, the pressure may be used to vary the number of pins 116 engaging the catheter, and furthermore, to control the impact of this interaction. The number of pins 116 engaging the catheter 104 will also strongly depend on the geometry of the stent 102, and more particularly, the ratio of the gap area to the outer surface area covered by the struts 136.

To reduce the frictional effect of any interaction between the pins 116 and the catheter 104, the inner ends 134 of the pins may be rounded, chamfered or otherwise beveled. In other embodiments, it may remain desirable to have flat-ended pins. In various embodiments, the inner ends 134 of the pins may have larger diameters than the middle portions 132 of the pins 116. In this way, when the pressure in the chamber 124 is reduced and the elastic sheath is allowed to expand, the inner ends 134 of the pins 116 will remain on the inner side of the rigid tubular member 118. Alternatively, the middle portions 132 of the pins 116 may be reduced relative to the inner and outer portions of the pins to define a range of travel for the pins. In this way, the range of length of travel of each pin through the rigid tubular member 118 can be precisely controlled. More particularly, the middle portion 132 of each pin 116 may be reduced in diameter only along a relatively small length of the middle portion of the pin that passes through the tubular member 118, thereby only permitting motion of the pin along the length of the pin having the reduced diameter. Additionally, it should be noted that the lengths of the pins 116 should be appropriately chosen such that the pins are able to slide at least partially through the gaps 138 such that at least some of the pins will engage the sides of the struts 136. By way of example, pin lengths in the range of approximately 1 to 20 mm or larger may be suitable for many applications. However, it should be appreciated that the lengths of the pins 116 can be widely varied.

During the axial force measurement, when the catheter 104 is pulled by the test bench 112, at least some of the pins 116 will engage sides of the stent struts 136, as illustrated in FIGS. 2-3. The pins 116 exert a lateral force against the sides of the struts 136 that is sufficient to prevent further axial movement of the stent 102. The pins 116 and rigid tubular member 118 may be formed of a rigid material such that the pins do not break or bend during the measurement, and such that the holes 128 are not stretched or otherwise distorted during the measurement. By way of example, suitable materials include metals, metallic alloys, ceramics and hard polymers, among others. It should be noted, that in other embodiments it may be desirable for the pins 116 and/or the tubular member 118 to be formed of a material that permits some flexion of the pins. More specifically, it may be desirable for a pin 116 that makes contact with a strut 136 during a stent securement test to be able to bend around the strut and thus enter a gap 138 adjacent the strut.

Additionally, the gripping fixture 100 may be configured in a modular manner. More particularly, each gripping fixture 100 may be configured such that it may be coupled with one or more other gripping fixtures 100. In this manner, when laid end to end, the gripping fixtures 100 may be secured to one another. This modular approach, employing a system of independently pressurizable gripping fixtures 100, allows shorter gripping fixtures to be used in combination with one another in securing a stent that is longer than any one of the gripping fixtures taken singly. This inherently permits each gripping fixture 100 to be more universally applicable in securing the wide variety of stent lengths that are available.

Upon completion of the stent securement test, the pressure in the pressure chamber 124 may be decreased to room pressure. In embodiments where the elastic sheath 120 is an elastic tube having a consistent equilibrium shape, the elastic tube will naturally expand to its intrinsic shape. As a result, the elastic sheath 120 will actively retract the pins 116 from the stent 102. In an alternate embodiment, the pressure in the pressure chamber 124 may be decreased below room pressure such that an effectively negative pressure acts on the elastic sheath 120. In this way, the elastic sheath is actively expanded by the higher pressure of the room. In this embodiment, an elastic sheath 120 with a well-defined equilibrium shape having a consistent cross section is not required.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed. It will be apparent to one of ordinary skill in the art that many modifications and variations are possible in view of the above teachings.

By way of example, in the illustrated embodiment, the invention was described with reference to a balloon expandable stent. However, it will be apparent to one of skill in the art that the present invention may also find applicability in a stent securement test measuring the axial force required to remove a catheter from a self-expanding stent enclosed within a deployment sheath. In one such embodiment, the pins 116 may extend into depressions formed by the deployment sheath in the gaps 138 in between the stent struts 136.

Additionally, in some embodiments it may be desirable to include pins having a multitude of differing diameters. Given that the lattice of struts forming the stent may assume a variety of geometries, employing such a variety of pins may make the gripping fixture 100 more applicable to a greater variety of stents.

Moreover, although described in the context of a stent and stent securement testing, it should be appreciated that embodiments of the present invention may be utilized in a great many applications outside of stent securement testing. The described arrangement may be used to grip both larger and smaller workpieces. By way of example, a gripping fixture 100 may find applicability in gripping springs, coils, screws and other generally tubular structures having lengths and diameters both larger and smaller than those of stents.

The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A gripping fixture suitable for use in stent securement testing, the gripping fixture comprising:
   a housing that includes a chamber;
   a perforated tubular member positioned within the chamber;
   a multiplicity of substantially radially extending pins, each pin being slideable through an associated perforation in the tubular member; and
   a sheath that circumscribes outer ends of the pins, the sheath circumferentially surrounding the perforated tubular member and cooperating with the housing to define a pressure chamber, wherein the sheath is arranged to move outer ends of the pins causing the pins to slide radially through the perforated tubular member.

2. A gripping fixture as recited in claim 1, further comprising a pressure controller for controlling the pressure within the pressure chamber, whereby pressure applied in the pressure chamber acts on the sheath and may be used to cause at least some of the pins to engage a stent during the performance of a stent securement test to substantially hold the stent in place relative to the gripping fixture during the stent securement test.

3. A gripping fixture as recited in claim 2, wherein the stent includes a plurality of struts and wherein applying pressure in the pressure chamber causes at least some of the pins to pass into gaps between adjacent struts during the stent securement test.

4. A gripping fixture as recited in claim 1, wherein the sheath is formed of an elastic material.

5. A gripping fixture as recited in claim 1, wherein the stent is carried on a catheter, the catheter further including an expandable balloon suitable for deploying the stent.

6. A gripping fixture as recited in claim 1, wherein the housing includes a pressurized fluid inlet configured to release pressurized fluid into the pressure chamber, wherein when pressurized fluid is released into the pressure chamber the fluid pushes on the sheath causing the sheath to diametrically contract such that the sheath pushes on the outer ends of the pins.

7. A gripping fixture as recited in claim 6, wherein a pressure of the pressurized fluid is in the range of approximately 0 to 20 psi.

8. A gripping fixture as recited in claim 1, wherein the outer end of each pin has a diameter that is larger than a middle portion of the pin.

9. A gripping fixture as recited in claim 1, wherein the outer ends of the pins are attached to the sheath.

10. A gripping fixture as recited in claim 1, wherein an inner end of each pin has a diameter that is larger than a middle portion of the pin.

11. A gripping fixture as recited in claim 1, wherein the inner ends of the pins are rounded.

12. A gripping fixture as recited in claim 1, wherein a middle portion of each pin has a diameter in the range of approximately 0.05 to 3.0 mm.

13. A gripping fixture as recited in claim 1, wherein each pin has a length in the range of approximately 1 to 20 mm.

14. A gripping fixture as recited in claim 1, wherein the pins have a pin center to pin center spacing in the range of approximately 0.1 to 5.0 mm.

15. A gripping fixture as recited in claim 1, wherein the pins are formed from one selected from the group consisting of: a metal, a metallic alloy, a ceramic and a rigid polymer.

16. A gripping fixture as recited in claim 1, wherein the perforated tubular member is formed from a rigid material selected from the group consisting of: a metal, a metallic alloy, a ceramic and a rigid polymer.

17. A gripping structure comprising a plurality of adjacent gripping fixtures as recited in claim 1, wherein the gripping structure is configured to perform a stent securement test on a stent that is longer than a single gripping fixture.

18. A gripping fixture comprising:
    a housing that includes a chamber;
    a perforated tubular member positioned within the chamber;
    a multiplicity of substantially radially extending pins, each pin being slideable through an associated perforation in the tubular member; and
    a sheath that circumscribes outer ends of the pins, the sheath circumferentially surrounding the perforated tubular member and cooperating with the housing to define a pressure chamber, wherein the sheath is arranged to move outer ends of the pins causing the pins to slide radially through the rigid perforated tubular member.

19. A gripping fixture as recited in claim 18, further comprising a pressure controller for controlling the pressure within the pressure chamber, whereby pressure applied in the pressure chamber acts on the sheath and may be used to cause at least some of the pins to engage a workpiece to substantially hold the workpiece in place relative to the gripping fixture.

20. A gripping fixture as recited in claim 18, wherein the housing includes a pressurized fluid inlet configured to release pressurized fluid into the pressure chamber, wherein when pressurized fluid is released into the pressure chamber the fluid pushes on the sheath causing the sheath to diametrically contract such that the sheath pushes on the outer ends of the pins.

* * * * *